United States Patent [19]
Lotti et al.

[11] Patent Number: 6,080,134
[45] Date of Patent: Jun. 27, 2000

[54] EXPANDABLE PARENCHYMAL BOLT WITH LEVER ACTIVATION

[75] Inventors: Richard A. Lotti, Poway; Greig E. Altieri, San Diego, both of Calif.

[73] Assignee: Camino NeuroCare, Inc., San Diego, Calif.

[21] Appl. No.: 09/214,775

[22] PCT Filed: May 13, 1997

[86] PCT No.: PCT/US97/08322

§ 371 Date: Jan. 8, 1999

§ 102(e) Date: Jan. 8, 1999

[87] PCT Pub. No.: WO98/51214

PCT Pub. Date: Nov. 19, 1998

[51] Int. Cl.[7] .................................................. A61M 5/32
[52] U.S. Cl. .................. 604/175; 604/104; 604/174; 285/96
[58] Field of Search .............................. 604/20, 105, 107, 604/108, 109, 104, 177, 178, 513, 175; 606/54, 57, 71, 105, 218, 151; 411/34, 38, 354; 269/254 R, 901; 72/457; 248/226.11, 316.1; 285/216, 217, 338

[56] References Cited

U.S. PATENT DOCUMENTS

| | | | |
|---|---|---|---|
| 1,297,113 | 3/1919 | Domenico | 285/338 |
| 2,152,429 | 3/1939 | Cave | 285/338 |
| 4,438,773 | 3/1984 | Letterio | 128/748 |
| 4,572,212 | 2/1986 | Letterio | 128/748 |
| 4,805,634 | 2/1989 | Ulrich et al. | 128/748 |
| 4,903,707 | 2/1990 | Knute et al. | 128/748 |
| 4,993,425 | 2/1991 | Kronberg | 128/748 |
| 5,054,497 | 10/1991 | Kapp et al. | 128/748 |
| 5,217,451 | 6/1993 | Freitas | 606/1 |
| 5,273,529 | 12/1993 | Idowu | 604/49 |

FOREIGN PATENT DOCUMENTS

| | | | |
|---|---|---|---|
| 29 09 314 A1 | 11/1980 | Germany | E04G 15/06 |
| WO 83/03190 | 9/1983 | WIPO | A61B 5/00 |

*Primary Examiner*—Wynn Wood Coggins
*Assistant Examiner*—Jennifer Maynard
*Attorney, Agent, or Firm*—Fulwider Patton Lee & Utecht, LLP

[57] ABSTRACT

A low profile parenchymal bolt having a cap, a body, and a base with two rods located through the cap that the base. Levers are located at the cap and are interconnected with the rods. Moving the levers outwardly pulls the rods and base towards the cap compressing the body and causing its outer diameter to increase into contact with an opening in the skull of a patient to form a fluid-tight seal and fixing the bolt in position. A lumen permits mounting an instrument through the bolt and when the body is compressed, the lumen reduces in size thus clamping the instrument in place in the bolt and forming a fluid-tight seal. Through use of non-ferric materials, artifacts in MRI are reduced.

16 Claims, 5 Drawing Sheets

EXPANDABLE PARENCHYMAL BOLT WITH LEVER ACTIVATION

BACKGROUND

The invention relates generally to bolts used to establish a channel through biological tissue and in particular, to a parenchymal bolt used to mount an instrument, such as a catheter, into the cranium for biomedical sensing or other purposes.

It has been the practice for many years to monitor the intracranial pressure of patients suffering from severe brain injuries. If the pressure rises above a critical level, pressure in the brain should be relieved by draining fluid from the affected ventricle. Several different structures have been proposed and adopted for this purpose. A catheter or the like is one such structure and may be inserted directly into the brain to accomplish these tasks. However, insertion of a catheter has been a difficult and risky procedure and requires a high level of skill. Chief among the risks is the possibility of bacterial infection. As a general rule, once the catheter has been inserted, it must be left in place for several days, and this makes the prevention of such infection both critically important and more difficult to accomplish.

Additionally, once positioned, it is important that the catheter remain in the selected position during the entire sensing period. Should the catheter be inadvertently withdrawn from the proper position in the brain, pressure changes or temperature changes may not be sensed. If the catheter were being used to drain excess fluid, this drainage procedure may be interrupted should the catheter be partially or fully withdrawn from the skull. Movement of the patient, either on his own initiative or by others, contact with the catheter outside the patient, and other forces may put strain on the catheter shaft tending to pull it from its established position in the skull of the patient. On the other hand, the catheter must be mounted so that it can be removed from the patient when needed. For example, removal may be required for recalibration of a sensor or for replacement of a sensor or drainage catheter.

A structure or arrangement of some type is required to stabilize the catheter so that it does not move during its period of operation in the brain. Because sensing may extend over many days, as mentioned above, the stabilizing arrangement must be robust and must provide a sterile communication with the patient to reduce the chances of infection.

In one prior approach, it is possible to insert such a catheter surgically through an opening in the skull, routing the catheter underneath the scalp against the surface of the skull for a significant distance from the opening in the skull and thence through an opening in the scalp to the outside world. This isolates the opening in the skull from contact with the environment outside the scalp and thereby reduces the opportunity for infectious agents to enter the opening in the skull. This approach has been favorably received and significantly reduces the risk of infection. However, insertion of the catheter by this method is time consuming and requires considerable surgical skill. Additionally, should the hospital staff need to remove the catheter for some reason, such as for recalibration, a substantial amount of time is required to extract it from the skull, pull it from the scalp tunnel, and reinstall it or a replacement catheter.

A parenchymal bolt structure, such as that shown in U.S. Pat. No. 4,903,707 to Knute entitled VENTRICULAR CATHETER ASSEMBLY is a different approach and has been found to be extremely useful in stabilizing a catheter used to sense pressure in the brain of a patient. An incision through the scalp to the skull is made and then a hole is bored through the skull. The bolt is then screwed into the bore hole and thereby establishes a sterile environment that reduces the chances for infection and firmly anchors the bolt in place in the skull. Through the bolt is a channel for receipt of an instrument such as a pressure sensing catheter. A threaded cap forces a clamp into contact with the catheter shaft as the cap is screwed onto the bolt body to hold the catheter in position in relation to the clamp, the bolt, and to the skull of the patient.

Requirements of such a bolt are that it be rapidly installable in the skull and that it work efficiently across a wide variety of skull types, including the much thinner pediatric skulls. The smaller pediatric skulls have much less thickness and in some cases do not provide the amount of material for the threads of the screw-type bolts to securely fasten to. It has been found that in such cases, some screw-type bolts do not work as well. Additionally, such a bolt must provide a fluid seal between it and the skull and a fluid seal between it and the inserted instrument or instruments as well as be easy to manipulate.

As used herein, an "instrument" includes a sensing catheter, drainage catheter, or other device designed for introduction into a biological location.

Additionally, a fluid seal for forming a sterile connection with the inserted instrument should be located as close to the patient's skull as possible to lessen the risk of infection.

Hence, those skilled in the art have recognized the need for a parenchymal bolt that not only secures an instrument in a desired position in relation to the ventricle of a patient, but that also reduces the risk of infection to the patient, is easy to install, permits rapid removal of the instrument, and that works efficiently for a wide variety of skulls. A device that is simple and inexpensive in construction, is easy to use, and is useable in a wide variety of conditions is also the subject of a recognized need. The present invention fulfills these needs and others.

SUMMARY OF THE INVENTION

Briefly and in general terms, the present invention is directed to a low profile parenchymal bolt for fluid-tight installation into an opening in the skull. In one aspect, the bolt comprises an expandable body, a cap in contact with one end of the body, a base in contact with the other end of the body and an expansion activating device that interconnects the cap with the base and comprises a lever. Wherein, the expansion activating device causes the cap and base to move closer together when the lever is moved in a predetermined direction thereby causing the expandable body to increase its outer diameter make contact with the skull opening. The expansion activating device allows the cap and base to move farther apart when the lever is moved in a second predetermined direction thereby allowing the expandable body to decrease its outer diameter.

In another aspect in accordance with the invention, the expansion activating device comprises a rod that interconnects the cap with the base through a control lumen of the body, and the rod is connected to the lever such that moving the lever in a predetermined direction moves the rod and base toward the cap. In a more detailed aspect, the base comprises a threaded opening, the rod is threaded and engages the threaded opening of the base wherein the expansion activating device causes the rod to be pulled toward the cap thereby causing the cap and base to move closer together.

In yet another aspect according to the invention, the base comprises two threaded openings, two rods have threaded ends, the threaded ends of the rods being engaged with respective threaded openings in the base wherein the expansion activating device causes the rods to be pulled toward the cap thereby causing the cap and base to move closer together. Further, the expansion activating device comprises two levers, the two threaded rods are engaged with the base, and the rods are interconnected to respective levers wherein rotating the levers pulls the rods and base toward the cap.

In a further detailed aspect, the rods are pinned to the levers. Additionally, the levers each have cam surfaces that cause the rods and base to be moved towards the cap when the levers are rotated in a predetermined direction.

In yet another aspect, the bolt further comprises an instrument lumen having an inner diameter formed through the cap, the body, and the base and having a size for slidably accepting an instrument. Wherein moving the lever in a predetermined direction to compress the body causes the lumen to reduce in size thereby clamping the instrument in position and forming a fluid-tight seal.

In yet a further detailed aspect, the cap is larger in diameter than each of the body and the base. Further, the cap is larger in diameter than the opening in the skull.

These and other aspects and advantages of the present invention will become apparent from the following detailed description, taken in conjunction with the accompanying drawings, illustrating by way of example the principles of the invention.

DETAILED DESCRIPTION OF THE PREFERRED EMBODIMENTS

Figure 1:
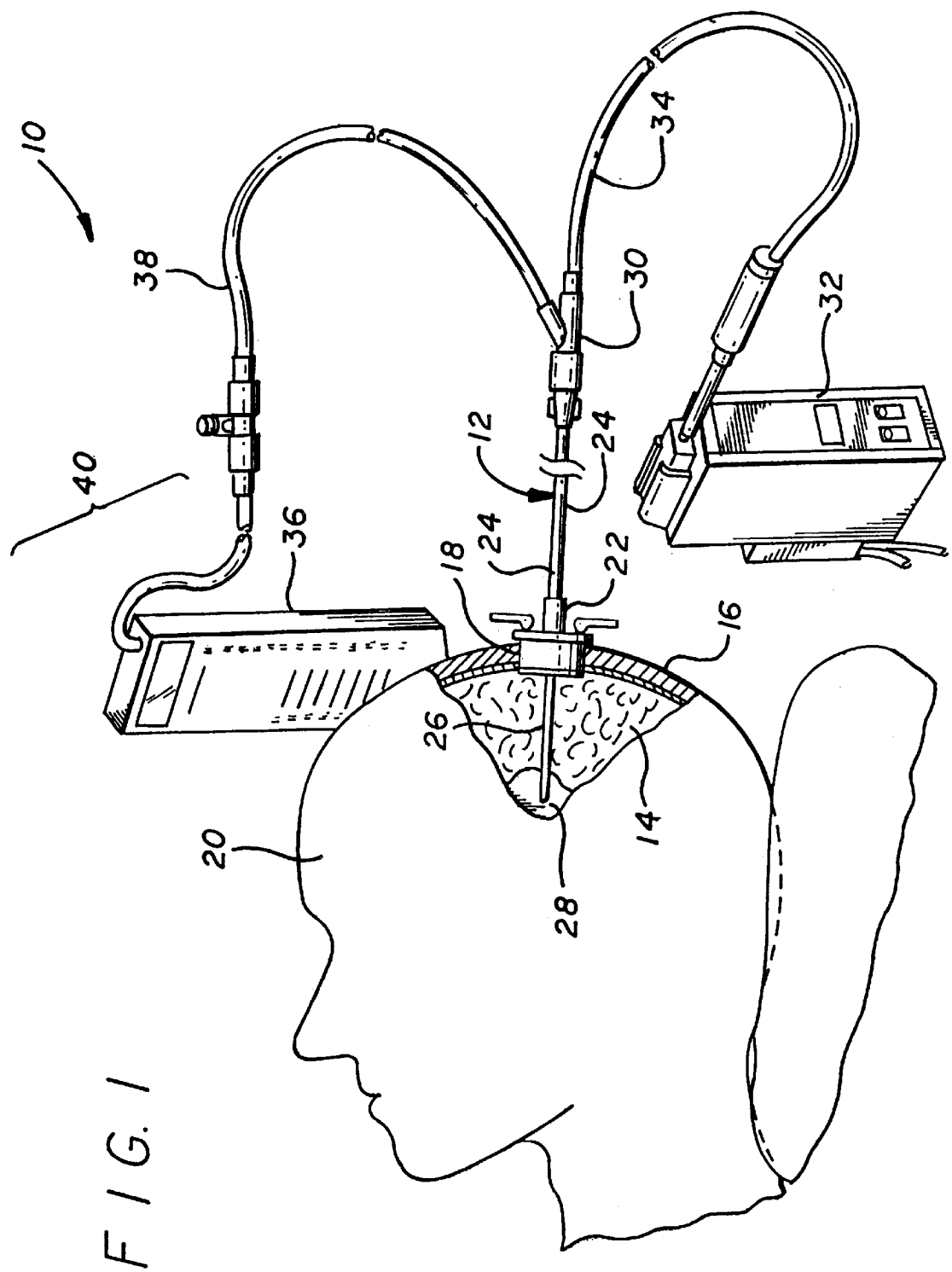
FIG. 1 presents an overall view of the use of a system for sensing pressure and temperature in the ventricle of a patient, and for draining fluid from that ventricle, using a low profile parenchymal bolt to mount a catheter in the skull of a patient in accordance with aspects of the invention.

In the following description, like reference numerals will be used to refer to like or corresponding elements in the different figures of the drawings. Referring now to FIG. 1 in more detail, there is shown a system 10 capable of monitoring a brain parameter of a living patient through an opening in the skull. Insertion of an instrument, in this case a catheter 12, into the brain 14 requires much surgical skill and has carried a significant risk of infection, especially when it has been necessary for the catheter to remain in position for an extended period of time. A catheter 12 shown in FIG. 1 can be quickly and easily inserted through the bolt 22 and forms a sterile connection with the skull 16 whereby the catheter can be left in place for a long period with the risk of infection greatly reduced.

In the case shown in FIG. 1, the catheter 12 comprises a ventricular catheter 12 designed generally for monitoring pressure in the brain and is inserted through an opening 18 in the skull 16 of a living person 20. A bolt 22 receives the catheter 12 and secures the catheter at a selected depth in the brain of the patient. The bolt 22 has a distal extremity adapted for sliding insertion into the opening 18 in the skull and is then expanded into contact with the opening, thereby securely mounting the bolt to the skull in a fluid tight relation. An elongated channel extends through the bolt 22 for receiving an instrument, such as the catheter 12, and as the bolt is expanded into contact with the opening 18, it also clamps the instrument into a fixed position in the bolt.

The catheter 12 in this case includes a portion protected by an outer protective sheath 24 adapted to fit slidingly within the channel of the bolt and a flexible portion 26 adapted to penetrate into a ventricle 28 of the brain. The flexible portion 26 has an opening from the lumen of the catheter to an exterior surface of the catheter for communication between the lumen and any fluid adjacent the catheter. Located in the distal end of this catheter is a pressure sensor (not shown) similar to that of U.S. Pat. No. 5,107,847 although different and/or additional sensors may be used.

Also shown in FIG. 1 are a coupling 30 and a monitor 32 connected to the coupling by a lead 34 containing optical fibers in this case. Also shown are a fluid collection vessel 36 and a drain tube 38 also connected to the coupling 30 that form a drain system 40 for draining fluid from the brain if necessary.

Figure 2:
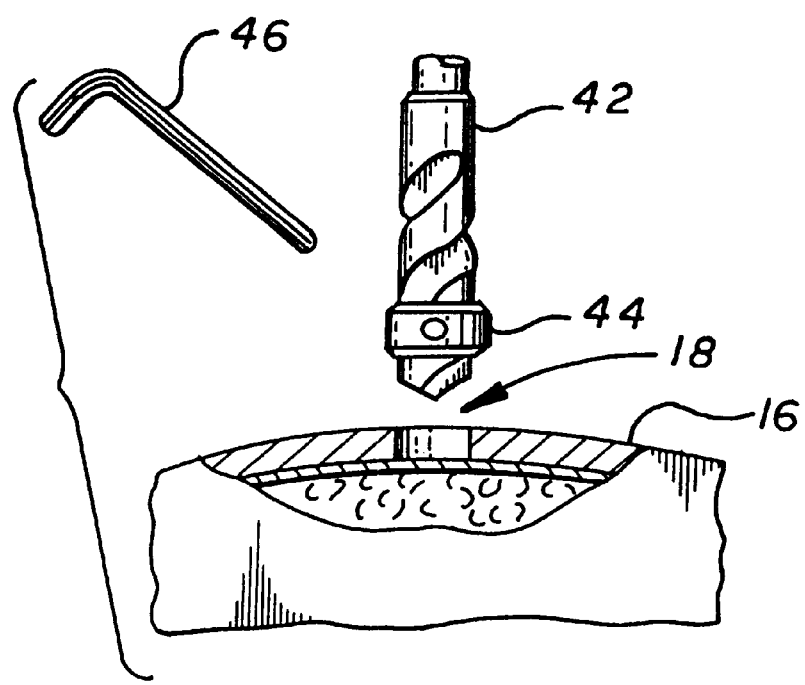
FIG. 2 shows a drill for boring a hole in the skull of a patient for insertion of a parenchymal bolt shown and described in detail below and for insertion of the catheter shown in FIG. 1.

Referring now to FIG. 2, an optional installation kit comprises a drill 42 for drilling an opening 18 through the skull 16 to receive the bolt, a drill stop 44 adapted for installation on the drill, an Allen wrench 46, for installing the drill stop at a selected location on the drill to fix a maximum depth to which the drill can penetrate. Other means may be used to form the opening 18 in the skull 16.

Figure 3:
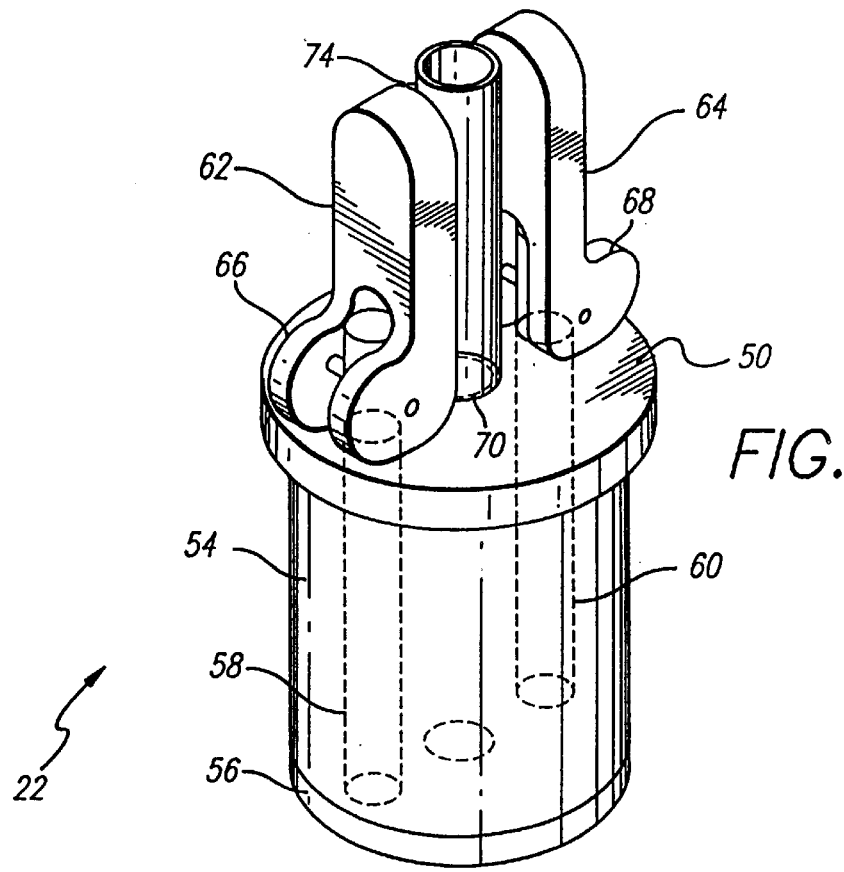
FIG. 3 is a perspective view of a low profile parenchymal bolt in accordance with certain aspects of the invention showing the levers oriented upwards and the bolt in a contracted configuration.

Referring now to the perspective view of FIG. 3, an embodiment of a low profile parenchymal bolt 22 in accordance with aspects of the invention is shown. A cap 50 is preferably larger than the bored opening 18 in the skull 16 of a patient (FIG. 1). A body 54 of resilient material is engaged with the cap 50 and a base 56 is disposed on the opposite side of the body 54 from the cap 50. The base 56 has approximately the same diameter as the body 54, both of which have diameters smaller than the cap diameter, in this embodiment.

An expansion activating device is included with the bolt 22 that controls the movement of the base and cap towards each other. As the cap and base approach each other, the body is compressed and expands outwardly increasing its outer diameter in direct proportion to the amount of movement of the base and cap towards each other. In this embodiment, the base 56 includes two threaded holes for accepting threaded rods 58 and 60. The two threaded rods 58 and 60 have unthreaded ends placed in openings formed in the cap 50 and protrude through control lumina in the body and into threaded engagement at their threaded ends with the base 56. At their proximal or cap ends, both rods 58 and 60 are pinned to respective cammed levers 62 and 64. Each lever includes a cam 66 and 68 respectively that engages the top surface of the cap when the levers are rotated outward. As the arms 62 and 64 are rotated outwardly, the cams 66 and 68 engage the top surface of the cap and cause the rods 58 and 60 to be pulled towards the cap thus pulling the base towards the cap and causing the body to expand outwardly increasing in diameter.

The rods 58 and 60 may be mounted to the base 56 in ways other than threading. For example, the rods may be welded to the base, swaged to the base, or press fit into holes in the base, or otherwise anchored to the base.

The cap, body, and base also include an additional lumen 70 for receipt of an instrument 72. A strain relief 74 is placed about the lumen 70 and extends proximally to protect sensitive parts of an instrument that is mounted in the bolt 22. In this case, the strain relief is tube-shaped and protects the instrument from bending damage. It also protects the instrument from the levers and their associated cams.

Figure 4:
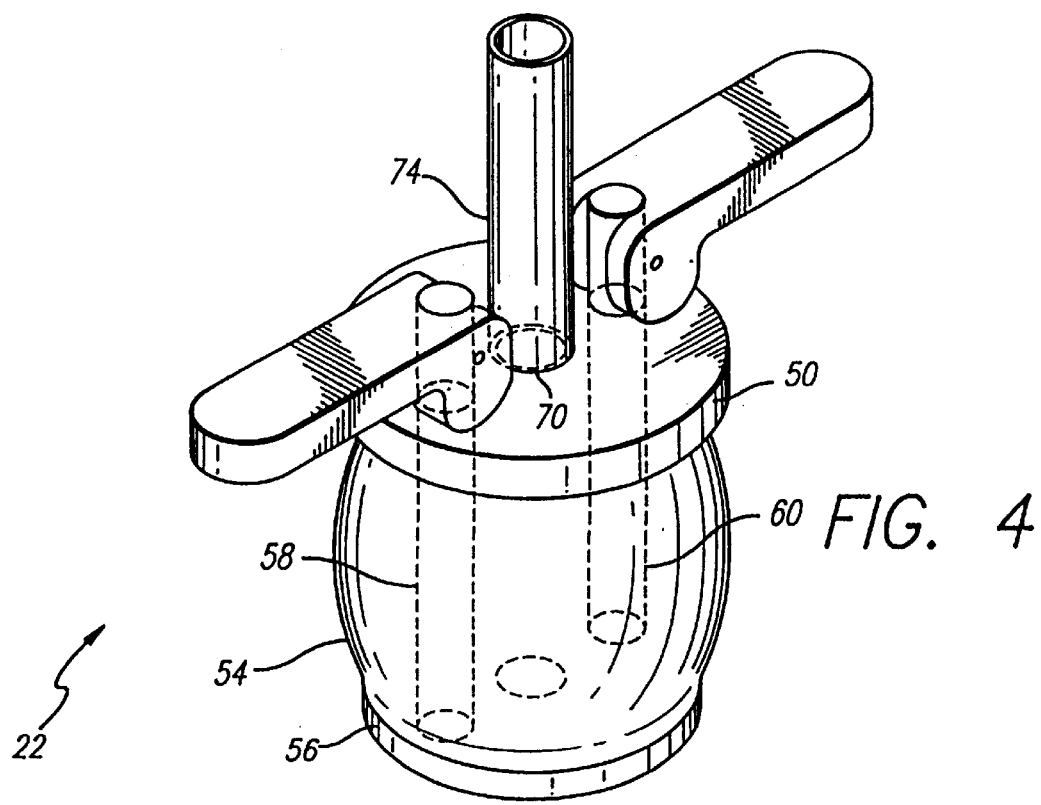
FIG. 4 is a perspective view of a low profile parenchymal bolt in accordance with certain aspects of the invention showing the levers oriented outward and the bolt in an expanded configuration.

Referring now to FIG. 4, the result of rotating the levers 62 and 64 outwardly is graphically shown. The base 56 moves toward the cap 50 as the levers are rotated outwardly. Such movement compresses the body 54 along its longitudinal axis and due to its resilience, the body expands outwardly thus increasing its outer diameter.

Figure 5:
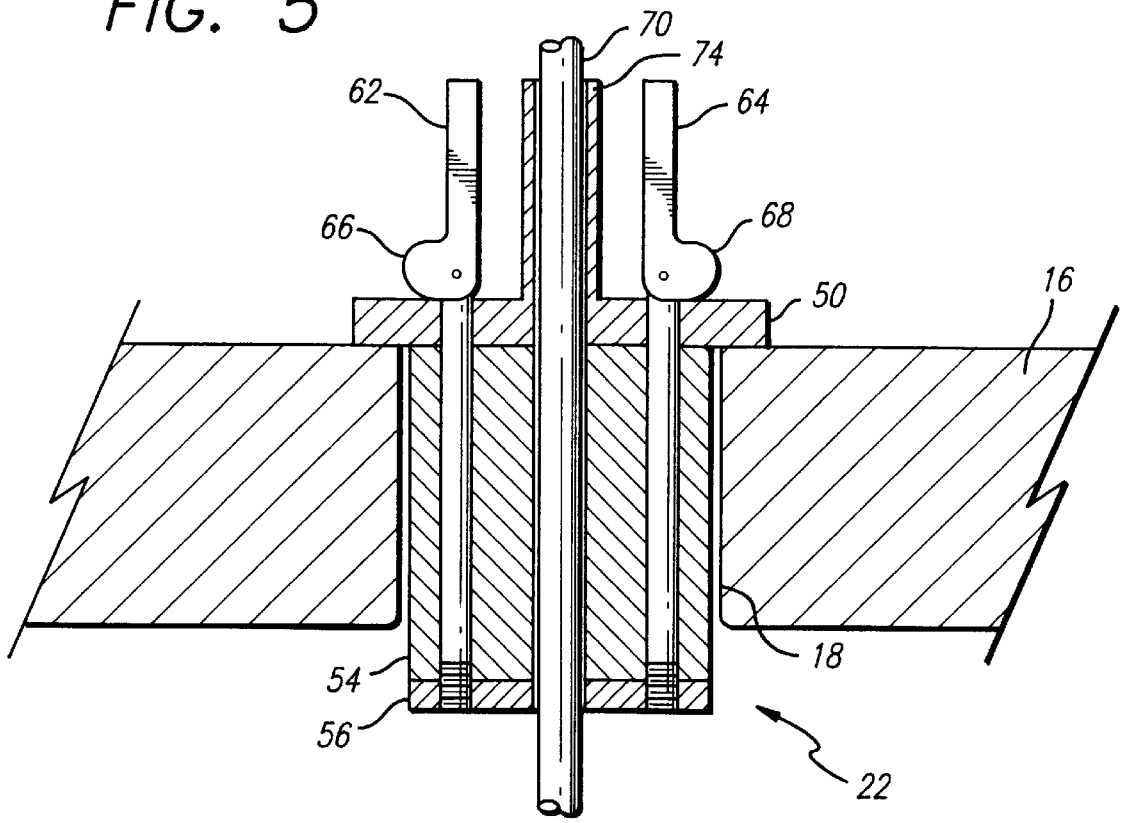
FIG. 5 presents an application of the bolt of FIG. 3 wherein an instrument has been mounted through the bolt and the bolt has been placed in position in the skull of a patient and is in the contracted configuration.
Figure 6:
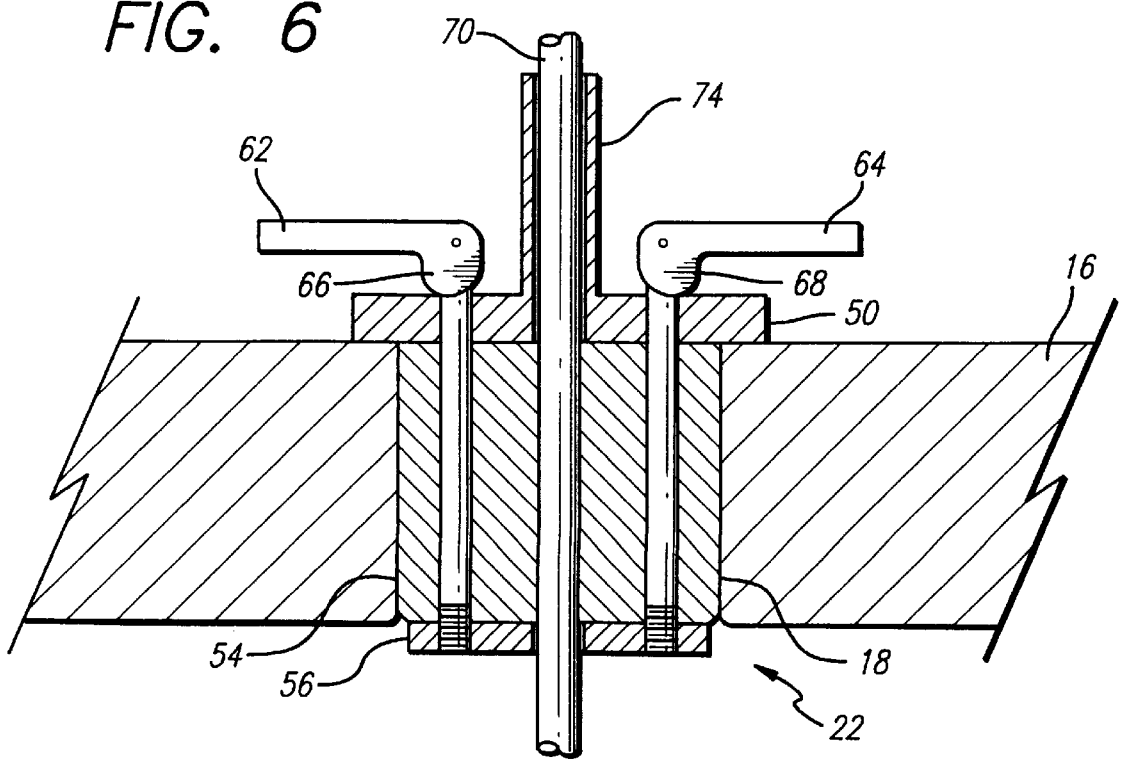
FIG. 6 presents the application of the bolt of FIG. 5 showing the bolt in the expanded configuration with both levers rotated outwardly and clamping the instrument with the strain relief.

The above effects are shown more clearly in the examples of FIGS. 5 and 6. Turning now to FIG. 5, an opening 18 has been formed in the skull 16 of a patient and the bolt 22 has been introduced such that the cap 50 is resting at the outer aperture of the opening. There is space between the body 54 of the bolt and the opening 18. Additionally, an instrument 72 has been placed in position through the bolt lumen 70. As can be seen, the bolt has some clearance in the opening of the skull. Additionally, the instrument has some clearance in the lumen 70 of the bolt so that the instrument can be placed as desired in the ventricle.

The levers 62 and 64 are now rotated outwardly as shown in FIG. 6 which pulls both rods 58 and 60 toward the cap and in turn, the base 56 is moved closer to the cap 50 causing the outer diameter of the body 54 to increase and make a fluid-tight contact with the opening 18 of the skull thus securing the bolt 22 in a fixed position with the skull 16. The action of compressing the body causes the body to reduce the size of its lumina about the rods and the instrument thereby forming a fluid-tight seal around these devices. Moving the levers in the opposite direction, i.e., upwards, will cause the bolt to return to the configuration shown in FIG. 5.

Figure 7:
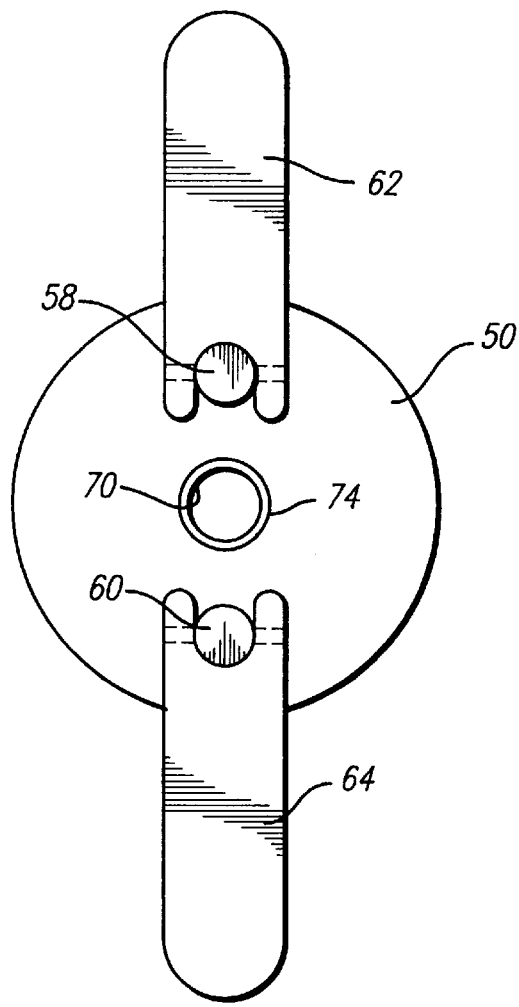
FIG. 7 presents a larger view of the cap of the bolt of FIG. 3 with the lever activators and the strain relief.
Figure 8:
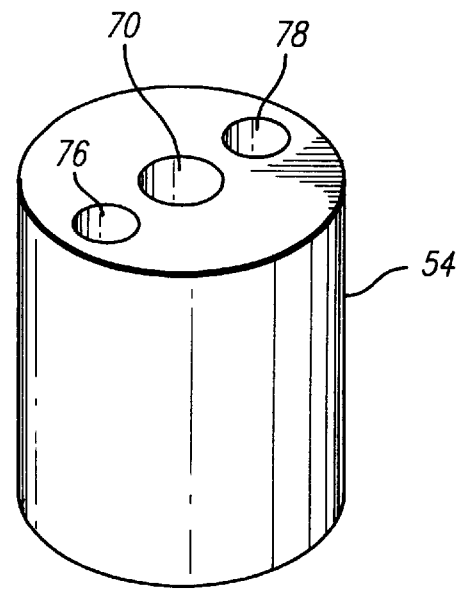
FIG. 8 presents a larger view of the body of the bolt of FIG. 3.
Figure 9:
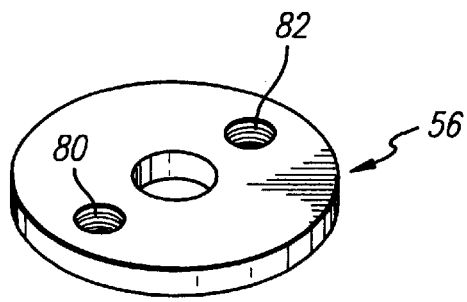
FIG. 9 presents a larger view of the base of the bolt of FIG. 3.

Referring now to FIGS. 7, 8, and 9, the cap 50, the body 54, and the base 56 are shown individually. The cap comprises the central lumen 70 and is shown with the strain relief 74 disposed about the lumen 70 to protect an installed instrument from bending damage. The cap is also shown with the two levers 62 and 64 pinned to the protruding rods 58 and 60, although they do not form part of the cap. The cap 50 and levers 62 and 64 as well as the threaded rods 58 and 60 may be formed of stainless steel or other biocompatible material. Should a bolt be desired that does not impart a significant MRI artifact, titanium may be substituted for the stainless steel of the components.

The body 54 shown in FIG. 8 comprises in this embodiment the control lumina 76 and 78, and the instrument lumen 70, all of which extend completely through the body. The body is formed in one embodiment of silicon but may be made of other biocompatible materials.

The base 56 is also formed stainless steel or other biocompatible material and includes the threaded holes 80 and 82 for accepting the threaded rods 58 and 60. An opening 84 for an instrument is also shown.

As is apparent from a review of FIG. 6, the size of the cams of each arm controls the amount of compression of the body 54 which in turn controls the amount of increase of the outer diameter of the body. The length of the cam controls how far the threaded rods are pulled through the cap thus limiting the increase in the outer diameter of the body. Making the cams shorter will result in a lesser increase in the outer diameter of the body while making the cams longer will result in a greater increase in the diameter of the body.

Thus, in accordance with the embodiments shown and described herein and referring again to FIG. 1, the physician can slide the catheter back and forth through the lumen 70 of the bolt 22 to position the flexible portion of the catheter in a desired location in the ventricle of the brain and then establish both a clamping of the catheter in position in the bolt and a fluid seal at the distal end of the bolt with the skull by simply rotating the levers in the appropriate direction. Additionally, the levers provide excellent handles for controlling the bolt during installation in the opening of the skull and during the installation of the instrument through the bolt and into the patient.

In operation, a physician makes an incision through the scalp and uses the drill and drill stop to drill an opening 18 through the skull 16 at a desired location. Then the bolt 22 is slid into the opening 18 until the cap 50 rests on the scalp. Next, a stylet (not shown) is inserted into the catheter 12 and the catheter is inserted through the lumen in the bolt 22 and positioned by the physician in the ventricle 28. The stylet is removed and next, the levers 62 and 64 are rotated outwardly causing the body 54 to expand outwardly into tight contact with the opening 18, fixing the bolt 22 in position in the opening 18 and also pressing the strain relief tightly against the catheter 12 thereby constraining it against movement relative to the bolt. Finally, the monitor 32 and, if needed, the drain means 40 are connected to the catheter 12 through the coupling 30.

Because the bolt in accordance with the invention does not rely on threaded engagement with the skull but instead uses outward expansion to lodge the bolt in position, the bolt is well suited for use in pediatrics where the skull is thin and not well adapted to receive a threaded engagement. However, the bolt is suited for other skulls as well and provides for rapid, yet efficient, engagement with the skull. Because of the seals made with the skull and with an instrument mounted through the bolt, the risk of infection is lowered.

Although certain specific embodiments of the invention have been described and illustrated, the invention is not to be limited to the specific forms or arrangement of parts so described and illustrated, and various modifications and changes can be made without departing from the scope and spirit of the invention.

What is claimed is:

1. A bolt for insertion into an opening in a skull, the bolt comprising:

an expandable body having an instrument lumen, the lumen having an inner diameter having a size for slidably accepting an instrument;

a cap in contact with one end of the body;

a base in contact with another end of the body; and an expansion activating device that interconnects the cap with the base and comprises a lever, wherein the expansion activating device causes the cap and base to move closer together when the lever is moved in a predetermined direction thereby causing the expandable body to increase its outer diameter and decrease the diameter of the instrument lumen wherein an instrument received in the instrument lumen is clamped in the lumen by the expandable body, and the expansion activating device allows the cap and base to move farther apart when the lever is moved in a second predetermined direction thereby allowing the expandable body to decrease its outer diameter and increase the diameter of the instrument lumen wherein an instrument received in the instrument lumen can slide in the lumen;

whereby when the expansion activation device is engaged, the outer diameter of the body makes contact with the skull opening.

2. The bolt of claim 1 wherein:

the expansion activating device comprises a rod that interconnects the cap with the base through a control lumen of the body; and the rod is connected to the lever such that moving the lever in a predetermined direction moves the rod and base.

3. The bolt of claim 2 wherein:

the base comprises a threaded opening;

the rod is threaded and engages the threaded opening of the base;

wherein the expansion activating device causes the rod to be pulled toward the cap thereby causing the cap and base to move closer together.

4. The bolt of claim 2 further comprising:

two rods engaged with the base;

wherein the expansion activating device causes the rods to be pulled toward the cap thereby causing the cap and base to move closer together.

5. The bolt of claim 4 wherein:

the expansion activating device comprises two levers;

the two rods engaged with the base are also interconnected with respective levers;

wherein rotating the levers pulls the rods and base toward the cap.

6. The bolt of claim 5 wherein the rods are pinned to the levers.

7. The bolt of claim 5 wherein the levers each have cam surfaces that cause the rods and base to be moved towards the cap when the levers are rotated in a predetermined direction.

8. The bolt of claim 7 wherein the cam surfaces interact with the cap to move the rods and base toward the cap.

9. The bolt of claim 2 wherein the lever has a cam surface that causes the rod and base to be moved towards the cap when the lever is rotated in a predetermined direction.

10. The bolt of claim 9 wherein the cam surface interacts with the cap to move the rod and base toward the cap.

11. The bolt of claim 1 further comprising:

an instrument lumen having an inner diameter formed through the cap, the body, and the base and having a size for slidably accepting an instrument;

wherein moving the lever in a predetermined direction decreases the inner diameter of the instrument lumen.

12. The bolt of claim 1 further comprising a strain relief located at the cap in close proximity to the instrument lumen.

13. The bolt of claim 1 wherein the cap is larger in diameter than each of the body and the base.

14. A bolt for insertion into an opening in a skull and for receiving and clamping an instrument also intended to be inserted into the opening in the skull, the bolt comprising:

an expandable body having an instrument lumen, the lumen having an inner diameter having a size for slidably accepting an instrument;

a cap in contact with one end of the body, the cap being larger in diameter than the opening in the skull, the cap having a cap aperture aligned with the lumen of the expandable body;

a strain relief located at the cap in alignment with the cap aperture such that an instrument inserted through the aperture will be engaged by the strain relief;

a base in contact with another end of the body; and an expansion activating device that interconnects the cap with the base and comprises a lever, wherein the expansion activating device causes the cap and base to move closer together when the lever is moved in a predetermined direction thereby causing the expandable body to increase its outer diameter and decrease the diameter of the instrument lumen wherein an instrument received in the instrument lumen is clamped in the lumen by the expandable body, and the expansion activating device allows the cap and base to move farther apart when the lever is moved in a second predetermined direction thereby allowing the expandable body to decrease its outer diameter and increase the diameter of the instrument lumen wherein an instrument received in the instrument lumen can slide in the lumen.

15. The bolt of claim 14 wherein the base comprises a base aperture aligned with the lumen of the expandable body, wherein an instrument inserted through the cap aperture and the body lumen may also be inserted through the base aperture and thereby extend completely through into the bolt.

16. The bolt of claim 15 further comprising:

two rods interconnecting the cap with the base through lumina formed in the body;

two levers connected to the rods such that moving the levers moves the base and cap in relation to each other.

* * * * *

UNITED STATES PATENT AND TRADEMARK OFFICE
CERTIFICATE OF CORRECTION

PATENT NO.  : 6,080,134
DATED         : June 27, 2000
INVENTOR(S) : Richard A. Lotti, Greig E. Altiera It is certified that error appears in the above-identified patent and that said Letters Patent is hereby corrected as shown below:

<u>Column 8,</u>
Line 13, claim 13, change "1", to read -- 12 --.

Signed and Sealed this

Second Day of October, 2001

*Attest:*

NICHOLAS P. GODICI
*Attesting Officer*    *Acting Director of the United States Patent and Trademark Office*